United States Patent [19]

Kobayashi et al.

[11] Patent Number: 4,961,835

[45] Date of Patent: Oct. 9, 1990

[54] SOLID ELECTROLYTE, SENSOR THEREWITH AND METHOD OF MAKING SAID SENSOR

[75] Inventors: Shouzo Kobayashi; Hiroshi Takagi; Yukio Sakabe, all of Nagaokakyo, Japan

[73] Assignee: Murata Manufacturing Co., Ltd., Japan

[21] Appl. No.: 330,603

[22] Filed: Mar. 29, 1989

[51] Int. Cl.$^5$ .......................................... G01N 27/409
[52] U.S. Cl. ................................. 204/427; 204/421; 204/424; 204/426; 501/103
[58] Field of Search ............... 501/103; 204/421, 1 S, 204/424, 426, 427

[56] References Cited

U.S. PATENT DOCUMENTS 4,328,294  5/1982  Tanaka et al. ..................... 429/193

FOREIGN PATENT DOCUMENTS 72681    4/1986  Japan ................................. 501/103
2149773  6/1985  United Kingdom ............... 501/103

*Primary Examiner*—G. L. Kaplan
*Attorney, Agent, or Firm*—Ostrolenk, Faber, Gerb & Soffen

[57] ABSTRACT

Solid electrolytic substance comprises yttrium oxide ($Y_2O_3$), silicon dioxide ($SiO_2$) and zirconium oxide ($ZrO_2$), and when represented by a general formula of $aY_2O_3 \cdot bSiO_2(1-A-b)ZrO_2$, a and b are respectively within a range of $0.012 \leq a \leq 0.122$ and $0.088 \leq b \leq 0.385$, showing a thermal expansion coefficient close to that of non-electrolytic ceramic (alumina).

13 Claims, 1 Drawing Sheet

SOLID ELECTROLYTE, SENSOR THEREWITH AND METHOD OF MAKING SAID SENSOR

BACKGROUND OF THE INVENTION

1. Field of the Invention

The present invention relates to solid electrolytic substances, particularly, to solid electrolytic substances having a good conductivity of oxygen ions. Such substances are advantageously used in an oxygen sensor which takes advantage of the potential differences produced in response to the movement of oxygen ions when they contact a substance having different oxygen partial pressures at its opposite sides such substances are also advantageously used in an oxygen pump, fuel cell etc. which take advantage of the movement of oxygen ions in response to the application of electric current thereto.

2. Description of the Prior Art

In an oxygen sensor used to measure the oxygen partial pressure in the high temperature range of, for example, 500°~1500° C., solid electrolytic substances made of $ZrO_2$ having $Y_2O_3$ or CaO and MgO added thereto have been used. Such sensors are used in connection with two measuring methods.

One measuring method is called a sampling method, wherein a gas to be measured is introduced into a measuring apparatus through an induction pipe and is reheated to a temperature of ~1000° C. to allow sufficient reactions of the solid electrolytic substance therein.

The other measuring method is called the direct insertion method. In this method the solid electrolytic substances are used as a barrier between a gas to be measured and a standard gas, and are inserted directly into the gas to be measured.

In either method, the potential difference E of the standard gas and the gas to be measured is read by a potentiometer. The oxygen partial pressure of the gas to be measured is then calculated in accordance with the following Nernst equation:

$$E = \frac{RT}{4F} \cdot \ln \frac{P_{O_2}(R)}{P_{O_2}(S)} \quad \text{Eq. (1)}$$

where,

R=gas constant, T=absolute temperature,

F=Faraday constant, $P_{O_2}$ (R)=oxygen partial pressure of standard gas and $P_{O_2}$ (S)=oxygen partial pressure of gas to be measured.

In the sampling method, since gas to be measured is reheated to a constant temperature in the measuring apparatus, the oxygen partial pressure can be measured simply. However, while there is no problem if the oxygen partial pressure is not changed by such a temperature as adding $O_2$ to $N_2$, it is ineffective when the oxygen partial pressure is changed by such a temperature as adding $H_2O$ and $H_2$ to $N_2$.

With the oxygen sensor employed in the direct insertion method, the aforesaid problem is not encountered since the measurement is made directly. However, the more severe the measurement conditions, the shorter the life time of the sensor.

FIG. 2 is a sectional explanatory view showing an example of an oxygen sensor of a conventional direct insertion method which is a background of the present invention. The oxygen sensor 1 includes a pipe 2 sealed at one end and consists of solid electrolytic substances of $ZrO_2$ to which $Y_2O_3$ or CaO and MgO have been added. The pipe 2 has been provided with porous platinum electrodes 3a and 3b, baked onto its inner and outer surfaces respectively. In the oxygen sensor 1, a standard gas is introduced into the pipe 2, which is inserted into the gas to be measured to measure the oxygen partial pressure.

In the direct insertion method shown in FIG. 2, since the pipe 2 is inserted into the gas to be measured, it must be relatively long and is expensive to provide. Besides, in the conventional oxygen sensor 1 used in the insertion method shown in FIG. 2, the pipe 2 consisting of a solid electrolytic substance is susceptible to thermal shocks and its heat-resisting cycle is short with the result that its frequency of failure is very high.

An oxygen sensor has also been devised in which an oxygen sensor chip comprising a columnar element consisting of solid electrolytic substances of $ZrO_2$ added with $Y_2O_3$ or CaO and MgO, and formed with porous platinum electrodes on its opposite end faces, is adhered or fused to the end portion of a non-electrolytic ceramic pipe. In such an oxygen sensor a non-electrolytic ceramic pipe, for example, an alumina pipe, mullite pipe etc. was used which is very hard at high temperatures. A pipe consisting of solid electrolytic substances was not used so that the pipe could, be manufactured at low cost and would result in a low frequency of failure. However, a problem arose due to the difference in thermal expansion coefficients between the ceramic pipe (non-electrolyte) and the oxygen sensor chip (solid electrolytic substance). The difference in thermal expansion coefficients caused cracks to occur after repeated use which could deteriorate the airtightness and disturb the accuracy of the measurement of the oxygen partial pressure.

SUMMARY OF THE INVENTION

It is, therefore, a primary object of the present invention to provide a solid electrolytic substance capable of being used to form an oxygen sensor which is resistant to cracks, and which can be used as a material for an oxygen sensor chip formed on the end portion of a non-electrolytic ceramic pipe.

The present invention relates to a solid electrolytic substance comprising yttrium oxide ($Y_2O_3$), silicon dioxide ($SiO_2$) and zirconium oxide ($ZrO_2$) in which when represented by a general formula of $aY_2O_3 \cdot bSiO_2 \cdot (1-a-b)ZrO_2$, a and b are within a range of $$0.012 \leq a \leq 0.109$$

$$0.129 \leq b \leq 0.385.$$

The thermal expansion coefficient of the solid electrolytic substance becomes about $10 \times 10^{-6}$ cm/° C.~$6.2 \times 10^{-6}$ cm/° C., which is close to that of non-electrolytic ceramics.

According to the present invention, since the thermal expansion coefficient of the solid electrolytic substance approaches that of the non-electrolytic ceramics, the solid electrolytic substance can be used as a material for an oxygen sensor chip and can be formed on the end portion of a non-electrolytic ceramic pipe. As a result an oxygen sensor can be manufactured which induces little thermal shock and results in a small amount of cracks.

In addition, in the oxygen detection and operating temperature on the lower temperature side of the solid electrolytic substance hardly change as compared to a conventional solid electrolytic substance of $ZrO_2$ added with $Y_2O_3$ or CaO and MgO. Accordingly, by adhering or fusing an oxygen sensor chip using the solid electrolytic substance according to the present invention onto the end portion of the non-electrolytic ceramic pipe, an oxygen sensor operating within the same temperature measuring range as an oxygen sensor using a conventional solid electrolytic substance can be manufactured.

Also in the solid electrolytic substance of the present invention, a thermal expansion coefficient can be selected within the range of about $10 \times 10^{-6}$ cm/° C. ~ $6.2 \times 10^{-6}$ cm/° C. without deteriorating the conductivity of oxygen ions. This inables it to be effectively used not only as a material for the oxygen sensor but also for an oxygen pump, a fuel cell and so on.

The above and other objects, features and advantages of the present invention will become more apparent from the following detailed description of the embodiment made in connection with the accompanying drawings.

DESCRIPTION OF THE PREFERRED EMBODIMENT

The raw materials, $ZrO_2$ and $Y_2O_3$ were first weighed respectively in mole % of 96: 4, 92:8 and 85:15. After being wet blended in a ball mill for 16 hours, they were then evaporated and dried to obtain powdered mixtures.

Next, the powdered mixtures were calcined at 1150° C. for 2 hours to obtain calcined materials.

Next, $ZrSiO_4$ was mixed with each calcined material to obtain each composition shown in table 1, to which 5 weight parts of vinyl acetate were added as a binder. The mixture was then subjected to wet blending and grinding in a ball mill for 16 hours to obtain pulverized materials. The resulting pulverized materials were dried by evaporation and sieved to obtain granular particles. The granular particles thus obtained were pressed at 2 ton/cm² by a dry press to form cylindrical bodies 20 mm long and 7.5 mm in diameter.

Next, the cylindrical bodies were held at 1600° C. in the air for 2 hours for firing to form fired products. To form oxygen sensor chips, on opposite end faces of the fired products thus prepared, platinum pastes were coated and baked at 1000° C. to form porous platinum electrodes.

Figure 1:
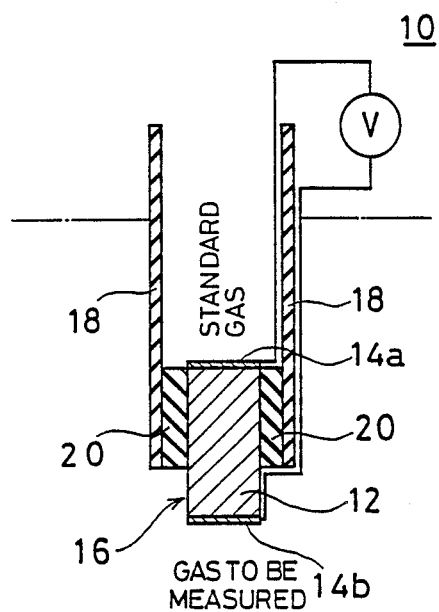
FIG. 1 is a cross-sectional view showing an oxygen sensor embodying the present invention.
Figure 2:
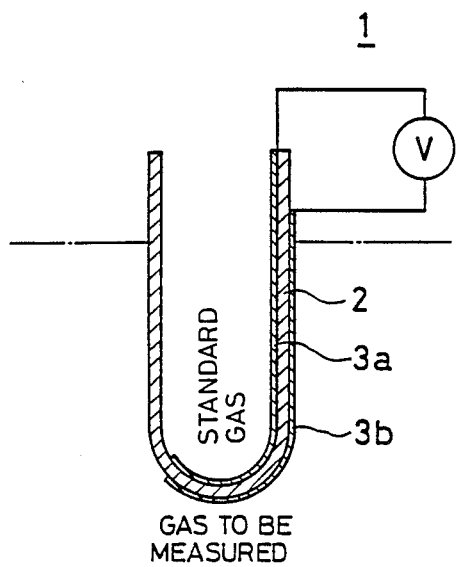
FIG. 2 is a cross-sectional view showing a conventional oxygen sensor.

Next, each oxygen sensor chip thus obtained was adhered to the end of an alumina non-electrolytic ceramic pipe with heat-resisting inorganic adhesives of alumina group. Each oxygen sensor chip was then heat treated to prepare the oxygen sensor 10 shown in FIG. 1 as specimens 1~19. As shown in FIG. 1, the oxygen sensor 10 comprises an alumina pipe 18 and an oxygen sensor chip 16. Porous platinum electrodes 14a and 14b are formed on opposite end faces of a cylindrical element 12 which consists of solid electrolytic materials.

The element 12 is then adhered to the end of the alumina pipe 18 with inorganic adhesives 20.

The alumina pipe 18 and the inorganic adhesives 20 both had a thermal expansion coefficient of $8.0 \times 10^{-6}$ cm/° C. The solid electrolytic substances of the oxygen sensor chip 16 of respective specimens 2~8 and 10~19 are composed of the three ingredients $ZrO_2$, $Y_2O_3$ and $SiO_2$ as shown in Table 1. These specimens are within the scope of the present invention.

The thermal expansion coefficient, low temperature operating temperature and life characteristics in different heat cycles were measured for respective specimens 1~19. The thermal expansion coefficients of the oxygen sensor chip were measured. The heat cycles included a first cycle in which the temperature was raised to 1400° C. from room temperature at a rate of 400° C. per hour, was held at 1400° C. for one hour, and then was dropped to 800° C. from 1400° C. at a rate of 400° C. per hour. In another heat cycle, the temperature was raised to 1400° C. from 800° C. at a rate of 400° C. per hour was held at 1400° C. for one hour, and then was dropped to 800° C. from 1400° C. at a rate of 400° C. per hour. The results of these measurements are shown in Table 2.

As is apparent from Table 2, the low temperature operating characteristics depends largely upon the molar ratio of $Y_2O_3$ in electrolytes of the solid electrolytic substances, a good low temperature operating characteristic is obtained at 4 to 15 mole %. A far better low temperature operating characteristic can be obtained at a molar ratio of 7~9 mole %.

It is clear that there is a correlation between the thermal expansion coefficient and life characteristics of the oxygen sensors of the present invention. The thermal expansion coefficient of the ceramic pipe and inorganic adhesives were assumed at $8.0 \times 10^{-6}$ cm/° C. This caused the life characteristics of the oxygen sensor using the solid electrolytic substance whose thermal expansion coefficient is close to those aforementioned to be outstanding. As such, when the thermal expansion coefficient of the solid electrolytic substance and those of the ceramic pipe and adhesives are matched, the life characteristics of the oxygen sensor is improved. In the solid electrolytic substances according to the present invention, the thermal expansion coefficient can be matched with those of the aforesaid ceramic pipe and inorganic adhesives, since it can be selected between $10 \times 10^{-6}$ cm/° C. and $6.2 \times 10^{-6}$ cm/° C.

When $SiO_2$ is more than 38.5 mole %, a decrease in the thermal expansion coefficient tends to slow down and the chip sintering and operating temperature are deteriorated as compared with the decreasing effect of the thermal expansion coefficient. Such composition does not fall within the scope of the present invention.

Also when mixing $SiO_2$, though it was added as $ZrSiO_4$ in the aforesaid embodiment, it may be added as $SiO_2$.

While the present invention has been described in detail and illustrated in the drawings, it is to be understood that such description is for illustration and exemplary purposes only and are not to be limiting. The spirit and scope of the present invention should, therefore, be determined solely by the scope of the appended claims.

TABLE 1

| Specimen No. | Electrolyte (wt %) | Nonelectrolyte (wt %) | Electrolyte $Y_2O_3$ (mole %) | $ZrO_2$ (mole %) | Composition $Y_2O_3$ (mole %) | $ZrO_2$ (mole %) | $SiO_2$ |
|---|---|---|---|---|---|---|---|
| 1 | 100 | 0 | 8 | 92 | 8.0 | 92.0 | 0 |
| 2 | 90 | 10 | 8 | 92 | 6.5 | 84.4 | 9.1 |
| 3 | 80 | 20 | 8 | 92 | 5.9 | 80.9 | 13.2 |
| 4 | 70 | 30 | 8 | 92 | 4.9 | 76.0 | 19.0 |
| 5 | 60 | 40 | 8 | 92 | 4.1 | 71.5 | 24.4 |
| 6 | 50 | 50 | 8 | 92 | 2.7 | 64.0 | 33.3 |
| 7 | 40 | 60 | 8 | 92 | 2.5 | 63.4 | 34.1 |
| 8 | 30 | 70 | 8 | 92 | 1.8 | 59.7 | 38.5 |
| 9 | 20 | 80 | 8 | 92 | 1.2 | 56.2 | 42.6 |
| 10 | 90 | 10 | 4 | 96 | 3.3 | 87.9 | 8.8 |
| 11 | 80 | 20 | 4 | 96 | 3.0 | 84.1 | 12.9 |
| 12 | 70 | 30 | 4 | 96 | 2.5 | 78.8 | 18.7 |
| 13 | 60 | 40 | 4 | 96 | 2.1 | 73.9 | 24.0 |
| 14 | 50 | 50 | 4 | 96 | 1.4 | 65.7 | 32.9 |
| 15 | 90 | 10 | 15 | 85 | 12.2 | 78.4 | 9.4 |
| 16 | 80 | 20 | 15 | 85 | 10.9 | 75.4 | 13.7 |
| 17 | 70 | 30 | 15 | 85 | 9.1 | 71.2 | 19.7 |
| 18 | 60 | 40 | 15 | 85 | 7.5 | 67.4 | 25.1 |
| 19 | 50 | 50 | 15 | 85 | 4.8 | 61.3 | 33.9 |

TABLE 2

| Specimen No. | Thermal Expansion Coefficient ($\times 10^{-6}$ cm/°C.) | Life Characteristics (Cycle) | Low Temperature Operating Temperature (°C.) |
|---|---|---|---|
| 1 | 10.50 | 2 | 680 |
| 2 | 9.68 | 5 | 680 |
| 3 | 8.65 | 20 | 680 |
| 4 | 8.08 | above 30 | 680 |
| 5 | 7.06 | 10 | 680 |
| 6 | 6.57 | 5 | 680 |
| 7 | 6.35 | 5 | 690 |
| 8 | 6.19 | 5 | 755 |
| 9 | 6.05 | 5 | 830 |
| 10 | 9.74 | 3 | 725 |
| 11 | 8.70 | 16 | 725 |
| 12 | 8.12 | above 30 | 725 |
| 13 | 7.21 | 14 | 725 |
| 14 | 6.58 | 4 | 730 |
| 15 | 9.61 | 6 | 740 |
| 16 | 8.54 | 23 | 740 |
| 17 | 7.97 | above 30 | 750 |
| 18 | 7.01 | 11 | 750 |
| 19 | 6.51 | 3 | 750 |

What is claimed is:

1. Solid electrolytic substance comprising yttrium oxide ($Y_2O_3$), silicon dioxide ($SiO_2$) and zirconium oxide ($ZrO_2$), in which when represented by a general formula of $aY_2O_3 \cdot bSiO_2 \cdot (1-a-b)ZrO_2$, a and b are respectively within a range of $0.012 \leq a \leq 0.109$ and $0.129 \leq b \leq 0.385$.

2. The solid electrolytic substance of claim 1 wherein said substance has a thermal expansion coefficient approximately between $10 \times 10^{-6}$ cm/° C. and $6.2 \times 10^{-6}$ cm/° C.

3. An oxygen sensor chip for use in an oxygen sensor, said chip being formed from a solid electrolytic substance comprising yttrium oxide ($Y_2O_3$), silicon dioxide ($SiO_2$) and zirconium oxide ($ZrO_2$), in which when represented by a general formula of $aY_2O_3 \cdot bSiO_2 \cdot (1-a-b)ZrO_2$, a and b are respectively within a range of:

$0.012 \leq a \leq 0.109$ and;

$0.129 \leq b \leq 0.385$.

4. The oxygen sensor chip of claim 3 wherein said oxygen sensor chip includes an elongated element composed of said solid electrolytic substance and having opposite end faces; and a pair of electrodes formed on said opposite end faces.

5. The oxygen sensor chip of claim 4 wherein said oxygen sensor chip is formed on the end of an elongated non-electrolytic ceramic member.

6. The oxygen sensor chip of claim 5 wherein said non-electrolytic ceramic member includes alumina.

7. The oxygen sensor chip of claim 5 wherein said non-electrolytic ceramic member includes mullite.

8. The oxygen sensor chip of claim 5 wherein said substance has a thermal expansion coefficient approximately between $10 \times 10^{-6}$ cm/° C. and $6.2 \times 10^{-6}$ cm/° C.

9. The oxygen sensor chip of claim 8 wherein said non-electrolytic ceramic member has a thermal expansion coefficient approximately between $10 \times 10^{-6}$ cm/° C. and $6.2 \times 10^{-6}$ cm/° C.

10. The oxygen sensor chip of claim 4 wherein said electrodes are porous platinum electrodes.

11. A method of manufacturing an oxygen sensor chip for use in an oxygen sensor comprising the steps of:

forming an elongated element having opposite end faces from a solid electrolytic substance including yttrium oxide ($Y_2O_3$), silicon dioxide ($SiO_2$) and zirconium oxide ($ZrO_2$) in which when represented by a general formula of $aY_2O_3 \cdot bSiO_2 \cdot (1-a-b)ZrO_2$, a and b are respectively within a range of:

$0.012 \leq a \leq 0.109$ and;

$0.129 \leq b \leq 0.385$;

forming an electrode on each of said opposite end faces; and forming said elongated element on an end of an elongated non-electrolytic ceramic member.

12. The method of claim 11 wherein said substance has a thermal expansion coefficient approximately between $10 \times 10^{-6}$ cm/° C. and $6.2 \times 10^{-6}$ cm/° C.

13. The method of claim 12 wherein said non-electrolytic ceramic member has a thermal expansion coefficient approximately between $10 \times 10^{-6}$ cm/° C. and $6.2 \times 10^{-6}$ cm/° C.

* * * * *